United States Patent
Park et al.

(10) Patent No.: US 7,913,572 B2
(45) Date of Patent: Mar. 29, 2011

(54) INTEGRATED MULTI-MEASUREMENT SYSTEM FOR MEASURING PHYSICAL PROPERTIES OF GAS DIFFUSION LAYER FOR POLYMER ELECTROLYTE FUEL CELL WITH RESPECT TO COMPRESSION

(75) Inventors: Gu-Gon Park, Daejeon (KR); Jin-Soo Park, Daejeon (KR); Min-Jin Kim, Daejeon (KR); Young-Jun Sohn, Daejeon (KR); Seok-Hee Park, Daejeon (KR); Sung-Dae Yim, Daejeon (KR); Tae-Hyun Yang, Daejeon (KR); Young-Gi Yoon, Daejeon (KR); Won-Yong Lee, Daejeon (KR); Chang-Soo Kim, Inchoen (KR)

(73) Assignee: Korea Institute of Energy Research, Daejeon (KR)

( * ) Notice: Subject to any disclaimer, the term of this patent is extended or adjusted under 35 U.S.C. 154(b) by 197 days.

(21) Appl. No.: 12/406,742

(22) Filed: Mar. 18, 2009

(65) Prior Publication Data

US 2010/0236335 A1    Sep. 23, 2010

(51) Int. Cl.
*G01N 3/08*    (2006.01)

(52) U.S. Cl. ............................ 73/818; 73/23.2; 73/23.29

(58) Field of Classification Search ............ 73/23.2, 73/23.29, 818
See application file for complete search history.

(56) References Cited

U.S. PATENT DOCUMENTS

| 5,419,828 A * | 5/1995 | Nakano et al. ............ 204/425 |
| 5,690,808 A * | 11/1997 | Akmal et al. ............ 205/775 |
| 7,137,301 B2 * | 11/2006 | Grudzien ................ 73/718 |
| 2003/0188968 A1 * | 10/2003 | Naito et al. ............ 204/424 |
| 2004/0086775 A1 * | 5/2004 | Lloyd et al. ............ 429/44 |
| 2007/0015043 A1 * | 1/2007 | Bai et al. ............ 429/44 |
| 2010/0136697 A1 * | 6/2010 | Kang et al. ............ 436/34 |

* cited by examiner

*Primary Examiner* — Max Noori
(74) *Attorney, Agent, or Firm* — Arent Fox LLP (57) ABSTRACT

Disclosed is an integrated multi-measurement system for measuring physical properties including thickness, electrical resistance and differential pressure of a gas diffusion layer for a polymer electrolyte fuel cell with respect to compression. The integrated multi-measurement system simultaneously measures changes in the physical properties of the gas diffusion layer depending on pressure upon measurement of the physical properties of the gas diffusion layer of the fuel cell and also measures through-plane permeability in which a gas is passed through a sample in a direction perpendicular to the sample and in-plane permeability in which a gas is passed through a sample in a direction parallel to the sample.

10 Claims, 6 Drawing Sheets

INTEGRATED MULTI-MEASUREMENT SYSTEM FOR MEASURING PHYSICAL PROPERTIES OF GAS DIFFUSION LAYER FOR POLYMER ELECTROLYTE FUEL CELL WITH RESPECT TO COMPRESSION

BACKGROUND OF THE INVENTION

1. Field of the Invention

The present invention relates to an integrated multi-measurement system for simultaneously measuring various physical properties, including thickness, electrical resistance, differential pressure and so on, with respect to compression, of a gas diffusion layer for a polymer electrolyte fuel cell.

2. Description of the Related Art

A fuel cell is a cell for directly converting chemical energy produced through oxidation of a fuel into electrical energy. A fuel cell, called a kind of power generator, is similar to a typical chemical cell in terms of the use of a redox reaction, etc. However, the fuel cell continuously receives reactants from the outside of the cell and continuously discharges reaction products to the outside of the cell, unlike the chemical cell where a cell reaction is performed in a closed system.

A variety of fuel cells using gaseous fuel including hydrogen and fossil fuel such as methane and natural gas and liquid fuel including methanol (methyl alcohol) and hydrazine have been devised. In particular, there are a low-temperature fuel cell which operates at a temperature of about 300° C. or lower and a high-temperature fuel cell which operates at a temperature above 300° C. Also, a high-temperature molten carbonate fuel cell for improving power generation efficiency without using a precious metal catalyst is referred to as a second generation fuel cell, and a solid electrolyte fuel cell exhibiting higher power generation efficiency is called a third generation fuel cell.

Examples of the fuel cell include a phosphoric acid fuel cell (PAFC), an alkaline fuel cell (AFC), a polymer electrolyte fuel cell (PEFC), a molten carbonate fuel cell (MCFC), and a solid oxide fuel cell (SOFC).

Figure 10:
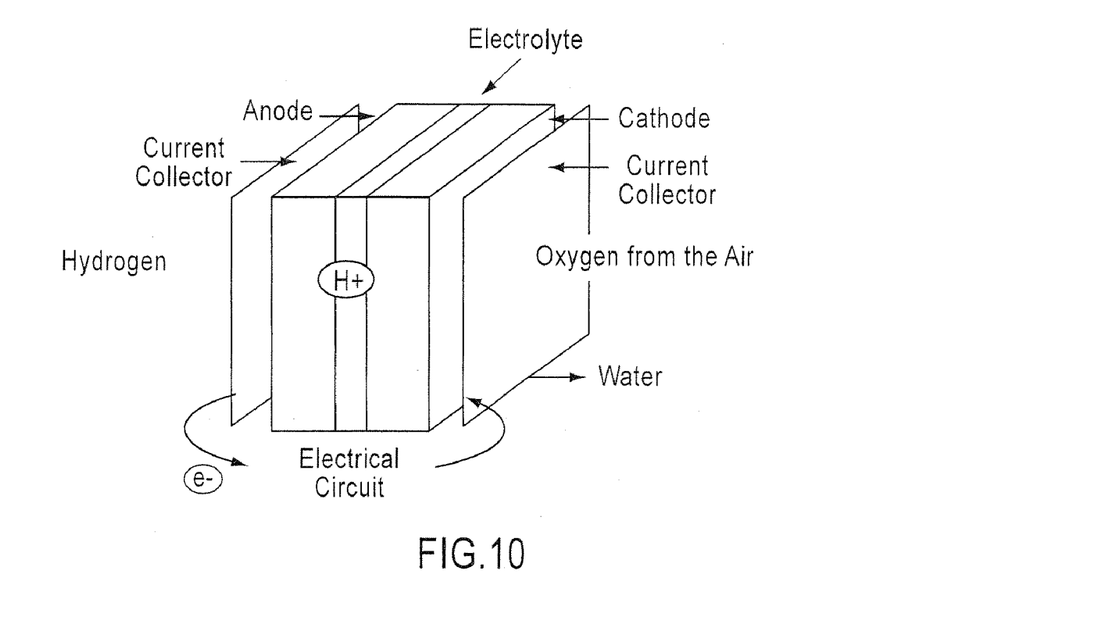
FIG. 10 shows a conventional PEFC.

Among fuel cell examples, the fuel cell related to the prevent invention is a PEFC. As shown in FIG. 10, a conventional PEFC is configured such that a porous anode and a porous cathode are respectively attached to both sides of a polymer electrolyte membrane and a gas diffusion layer is then further attached thereto.

Specifically, the main components of the PEFC include a polymer electrolyte membrane, electrodes (anode, cathode), a gas diffusion layer, and a separator for a stack. As such, two electrodes including the anode and the cathode are attached to the polymer electrolyte membrane through hot pressing, thus forming a membrane-electrode assembly (MEA). The construction and performance of the MEA are important to the PEFC.

A fuel cell stack is formed by stacking tens to hundreds of single cells respectively responsible for an electrochemical reaction. The single cell or the stack thereof is configured such that both end plates are tied with a tie rod or pneumatic pressure in order to reduce contact resistance between the components. Each end plate includes a reactive gas outlet, a reactive gas inlet, a cooling water circulation line, and a connector for electrical power output.

Figure 11:
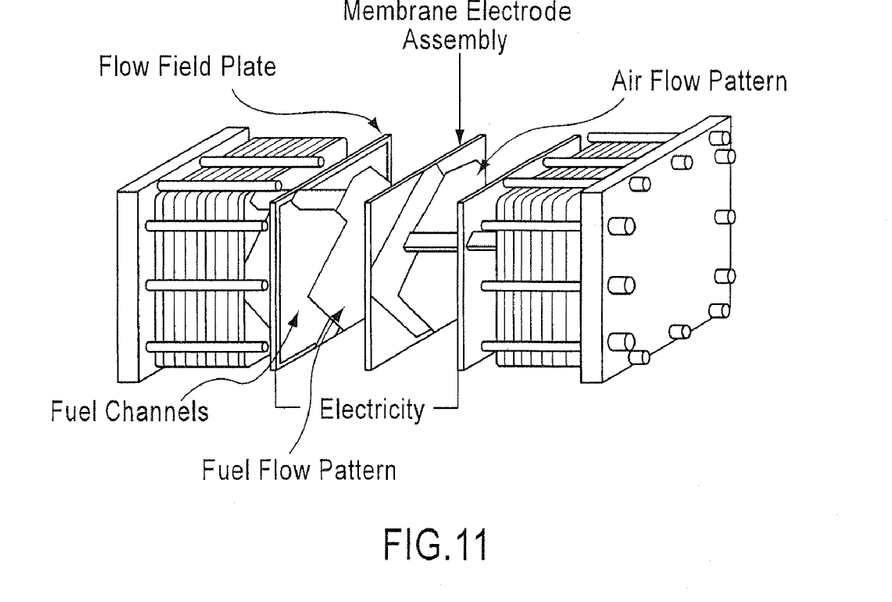
FIG. 11 shows a conventional PEFC stack.

FIG. 11 shows a PEFC stack made by Ballard. In addition to the stack, an actual system includes a fuel reformer, an air compressor, a heat/water treater, and a power converter.

The PEFC has advantages such as a high output density, a low operating temperature of 100° C. or less and high corrosion resistance of an electrolyte, and is also advantageous in terms of few limitations for a mounting place thereof, simplification of the equipment's structure, applicability to small-capacity equipment (having power of ones of kW), very safe operation repeatability (convenient operating safety), availability at room temperature and quick startup (for emergency and military power) Thus, the PEFC may be widely applied to various fields, including 250 kW industrial modules, tens of kW commercial applications, ones of kW residential applications, 80 kW automobiles, 150 kW buses, small fuel cells less than 1 kW, and subwatt IT products.

Figure 12:
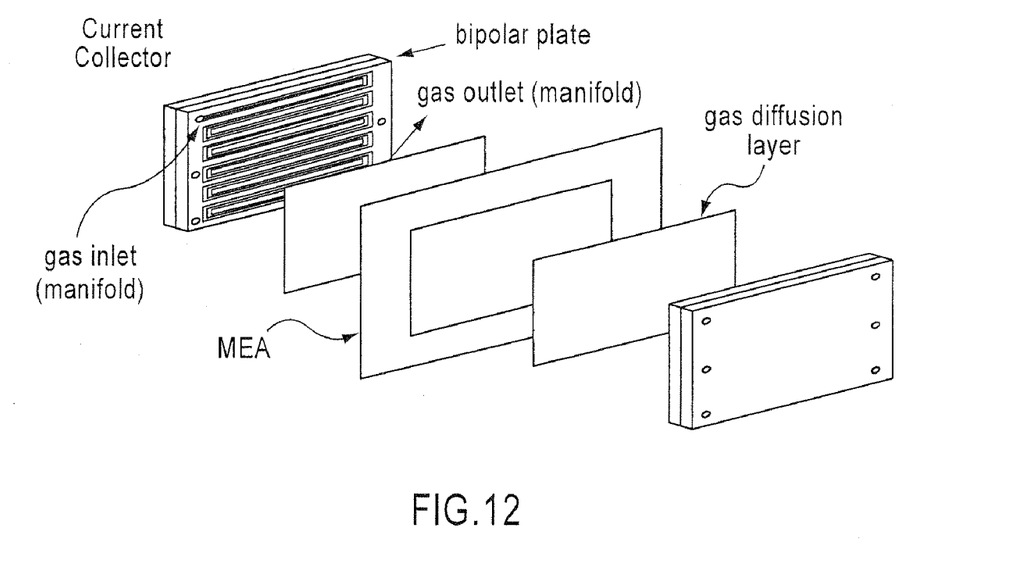
FIG. 12 is an exploded perspective view showing the conventional PEFC.

FIG. 12 is an exploded perspective view of the fuel cell of FIG. 10 or 11, in which a current collector is disposed at both ends of the fuel cell, an MEA is located at the center of the fuel cell, and a gas diffusion layer is disposed between the current collector and the MEA. Each current collector includes a separator, a gas inlet and a gas outlet.

In the single fuel cell, the gas diffusion layer plays a role as a pathway for transferring a reactive gas and water which is a product and performs thermal conduction and electrical conduction. Upon actual operation, because the gas diffusion layer is subjected to clamping pressure, there is a need to examine changes in physical properties occurring in the clamping state.

Also, because the effect of the degree of clamping pressure in the fuel cell on performance of the fuel cell is very great, optical clamping conditions must be found. Such optical clamping conditions may be found within optimal ranges of thickness, contact resistance and gas permeability with respect to compression.

SUMMARY OF THE INVENTION

The basic physical properties (thickness, contact resistance, gas permeability, compressibility and so on) of a gas diffusion layer are important parameters to be taken into consideration when designing and manufacturing a fuel cell stack. There exists an apparatus for measuring each of the basic physical properties. However, because the physical properties are simultaneously changed under actual stack clamping conditions, simultaneous measurement of the physical properties under actual clamping conditions rather than individual measurement thereof is essentially required to optimally design and manufacture the stack.

Also, a conventional measurement system measures only through-plane permeability in which a gas is passed through a sample in a direction perpendicular to the sample and does not measure in-plane permeability in which a gas is passed through a sample in a direction parallel to the sample. The in-plane permeability is important as the physical property of the gas diffusion layer itself, and, in particular, is used as a very important parameter to estimate bypass flow into the gas diffusion layer upon design of a separator and computer simulation. Upon operation of the fuel cell, in order to hydrate the polymer membrane, a moisture gas is supplied, and thus there is a need to understand gas flow properties of the gas diffusion layer depending on relative humidity.

Accordingly, the present invention has been made keeping in mind the above problems occurring in the related art, and an object of the present invention is to provide an integrated multi-measurement system for measuring physical properties including thickness, electrical resistance, differential pressure and so on of a gas diffusion layer for a PEFC with respect to compression, so as to simultaneously measure changes in the physical properties depending on clamping pressure upon measurement of the physical properties of the gas diffusion layer, and also measure through-plane permeability in which a gas is passed through a sample in a direction perpendicular to the sample and in-plane permeability in which a gas is passed through a sample in a direction parallel to the sample.

Another object of the present invention is to provide an integrated multi-measurement system for measuring physical properties of a gas diffusion layer of a polymer electrolyte fuel cell, which includes a device for controlling a temperature of the system and moisture content contained in a supplied gas so as to measure differential pressure of the gas diffusion layer depending on relative humidity.

According to the present invention, there is provided an integrated multi-measurement system for measuring physical properties including thickness, electrical resistance, differential pressure and so on of a gas diffusion layer for a polymer electrolyte fuel cell with respect to compression, including a motor and a rod for applying pressure to a gas diffusion layer sample; a plate descending by the pressure applied by the motor and the rod; a thickness gauge fixed on the plate and measuring a change in thickness of the gas diffusion layer sample depending on the pressure; an upper plated sheet which is pressed at an upper surface thereof by the plate and which comes into contact with a lower portion of the plate descending by the pressure applied by the motor and the rod to thus press the gas diffusion layer sample located under the upper plated sheet, the upper plated sheet having gas outlets formed in one or more surfaces of the upper plated sheet to discharge a gas passed through the gas diffusion layer sample to outside via an internal passage and a milliohm meter connection terminal formed at a position of a plated surface of the upper plated sheet; a lower plated sheet located under the upper plated sheet to thus support the pressure applied to the gas diffusion layer sample and having a gas inlet formed in one surface of the lower plated sheet to supply the gas to the gas diffusion layer sample so that the gas is discharged to the gas diffusion layer sample via an internal passage and a milliohm meter connection terminal formed at a position of the lower plated sheet; a milliohm meter wire-connected to the milliohm meter connection terminals respectively mounted to the upper plated sheet and the lower plated sheet so as to measure electrical resistance; and a control box including a load indicator, a motor speed controller, a load controller and a differential pressure gauge, in which the differential pressure gauge measures differential pressure for an in-plane and a through-plane of the gas diffusion layer sample pressed by the motor and the rod.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, a detailed description will be given of embodiments of the present invention with reference to the appended drawings.

Figure 1:
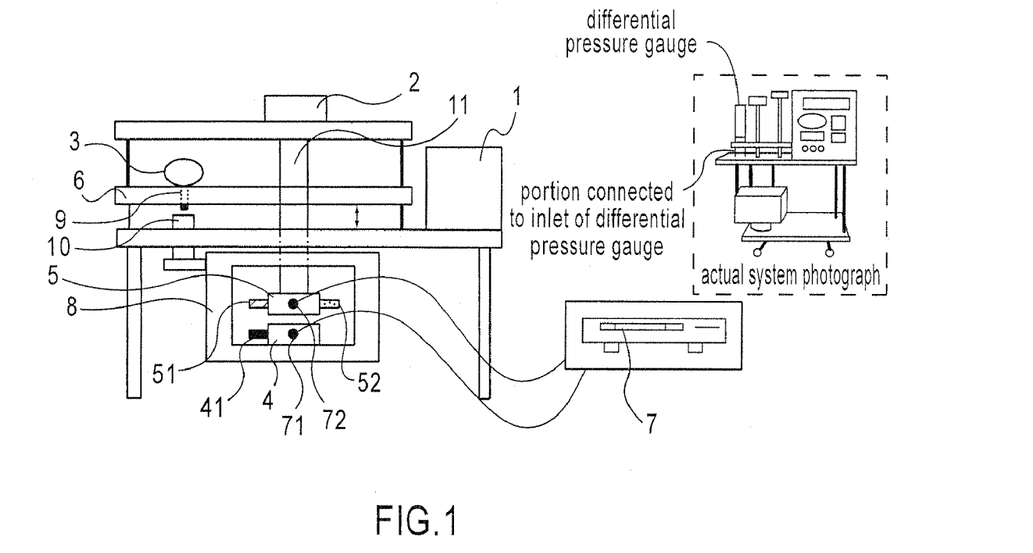
FIG. 1 schematically shows an integrated multi-measurement system according to the present invention.
Figure 2:
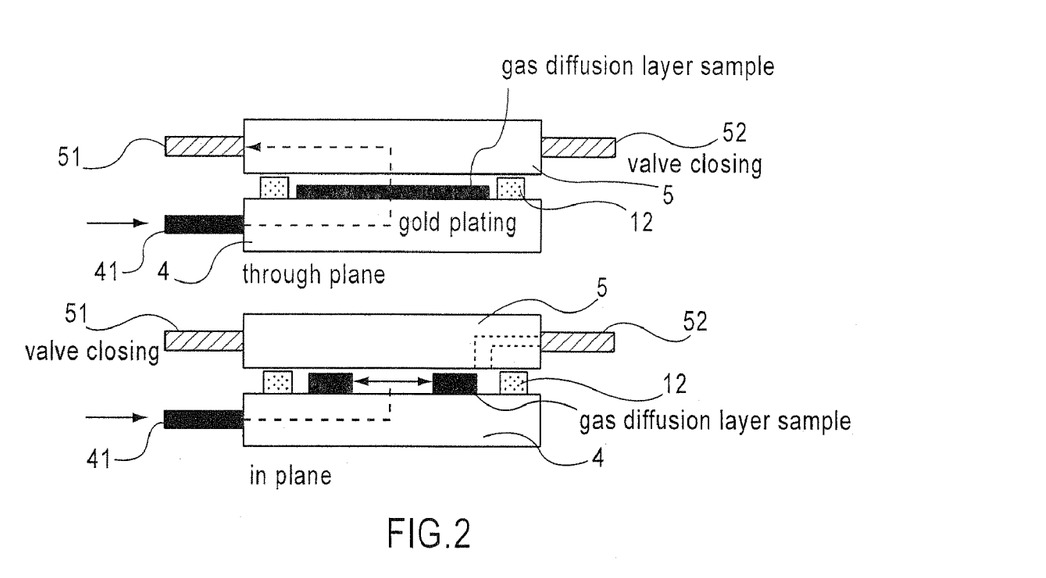
FIG. 2 schematically shows measurement of through-plane permeability before a gas is passed through a through-plane of a sample and measurement of in-plane permeability before a gas is passed through an in-plane of the sample.

FIG. 1 schematically shows an integrated multi-measurement system according to the present invention. FIG. 2 schematically shows measurement of through-plane permeability in which a gas is passed through a sample in a direction perpendicular to the sample and measurement of in-plane permeability in which a gas is passed through a sample in a direction parallel to the sample, according to the present invention. As shown in the drawing, the integrated multi-measurement system for simultaneously measuring physical properties including thickness, electrical resistance and differential pressure of the gas diffusion layer depending on clamping pressure includes a motor 2 and a rod 11 for applying pressure to a gas diffusion layer sample, and a plate 6 which descends by the pressure applied by the motor 2 and the rod 11 to thus press an upper surface of an upper plated sheet 5 and which has a thickness gauge fixed on an upper surface of the plate. The thickness gauge 3 is fixed on the plate 6 and measures a change in thickness of the gas diffusion layer sample depending on the pressure, and an upper plated sheet 5 comes into contact with a lower portion of the plate 6 descending by the pressure applied by the motor 2 and the rod 11 to thus press the gas diffusion layer sample located under the upper plated sheet, and has gas outlets formed in one or more surfaces thereof to discharge a gas passed through the gas diffusion layer sample to the outside via an internal passage and a milliohm meter connection terminal 72 formed at a position of the plated surface thereof so as to be connected to a milliohm meter 7. Further, a lower plated sheet 4 is located under the upper plated sheet 5 to thus support the pressure applied to the gas diffusion layer sample, and has a gas inlet 41 in one surface thereof to supply a gas to the gas diffusion layer sample so that the gas is discharged to the gas diffusion layer sample via an internal passage, and a milliohm meter connection terminal 71 formed at a position thereof so as to be connected to the milliohm meter 7. Furthermore, the milliohm meter 7 is wire-connected to the milliohm meter connection terminals 71, 72 respectively mounted to the lower plated sheet 4 and the upper plated sheet 5 so as to measure electrical resistance. Also, a control box 1 includes a load indicator, a motor speed controller, a load controller and a differential pressure gauge, in which the differential pressure gauge measures differential pressure for the in-plane and the through-plane of the gas diffusion layer sample pressed by the motor and the rod.

The gas outlets of the upper plated sheet 5 include a pair of gas outlets 51, 52 provided at both sides of the upper plated sheet so as to measure the differential pressure when passing the gas through the through-plane of the gas diffusion layer sample by opening of one of the pair of gas outlets and the differential pressure when passing the gas through the in-plane of the gas diffusion layer sample by opening of the other of the pair of gas outlets.

The opening or closing of the valve for the gas outlet 51, 52 is manually activated.

The upper and lower plated sheets are plated with gold in order to measure electrical resistance.

Specifically, when the valve for the gas outlet 51 of the upper plated sheet 5 is closed, the gas is supplied through the gas inlet 41 of the lower plated sheet 4, passed through the in-plane of the sample, and then discharged through the gas outlet 52. In this case, the differential pressure for the in-plane of the sample is measured. Also, when the valve for the gas outlet 52 of the upper plated sheet 5 is closed, the gas is supplied through the gas inlet 41 of the lower plated sheet 4, passed through the through-plane of the sample and then discharged through the gas outlet 51. In this case, the differential pressure for the through-plane of the sample is measured.

More specifically, the differential pressure in a direction perpendicular to the sample, namely a direction where the gas is passed through the through-plane of the sample, and the differential pressure in a direction parallel to the sample, namely, a direction where the gas is passed through the in-plane of the sample are measured. The gas inlet 41 is connected to a fuel cell station or a gas supply chamber including an MFC (mass flow controller), and a T-shaped tube is provided in the middle portion of a connection tube such that one side of the T-shaped tube is connected to the gas inlet 41 and the other side thereof is connected to the inlet of the differential pressure gauge in the control box. Depending on the range of the differential pressure, diverse differential pressure gauges may be used (e.g. 1000 mmH$_2$O~), and this component may be replaced, if necessary. The gas outlets 51, 52 are connected with tubes having valves at ends thereof. When a valve is opened, the gas may be exposed to the atmosphere.

Also, in order to simultaneously measure thickness, electrical resistance and differential pressure depending on relative humidity under predetermined temperature conditions, the upper plated sheet 5 and the lower plated sheet 4 are mounted in a water bath and an O-ring 12 is mounted around the gas diffusion layer sample to hermetically seal the sample, after which measurement in water is performed.

The reason why the system is mounted in the water bath is that the system is controlled and maintained at a predetermined temperature to adjust the relative humidity. The relative humidity is calculated using saturated water vapor pressure at the temperature of the supplied gas and the temperature of the system, and the temperature of the water bath is changed to thus control the relative humidity.

Alternatively, to control the temperature, the upper and lower plated sheets may be heated using an electrical heater.

Further, the lower plated sheet 4 may have a position mark for locating the gas diffusion layer sample thereon, and may also have an acrylic sheet having a semicircular shape used as a jig for more accurate alignment so that the sample is accurately located at a position.

The thickness gauge 3 according to the present invention has a resolution of 0.001 mm (1 µm) or more and measures a change in thickness depending on the pressure. The thickness gauge is mounted to pass through the plate. When the plate 6 descends, a flexible portion 9 of the thickness gauge 3 comes into contact with a contact part 10. How far the plate moves is displayed on the gauge. The method of measuring the thickness of the gas diffusion layer is described in detail below.

1) Depending on material properties of a sample, a standard thickness at a predetermined pressure is determined.

2) In the case of a gas diffusion layer, according to DIN 53855 a thickness under pressure of 25 kPa is determined as an initial thickness.

3) When a load of 25 kPa is applied, the plate 6 descends and upper and lower gold-plated sheets come into contact with each other, and thus how far the plate moves is displayed on a thickness gauge.

4) The value displayed on the gauge is set to zero.

5) The motor is switched to rotate in the reverse direction, thus removing the applied pressure.

6) A sample is disposed between the upper and lower gold-plated sheets.

7) When a load of 25 kPa is applied, the thickness of the sample is displayed on the gauge.

8) The load at this time is set to zero.

9) While desired pressure is being applied, a change in thickness of the sample is measured.

The thickness gauge having a resolution which can accurately and simply measure fine changes of ones of µm is used.

The gas diffusion layer sample disposed between the upper plated sheet 5 and the lower plated sheet 4 may be sized to have an outer diameter of 0.5~5 cm and an inner diameter of 0.3~4.5 cm. Namely, the size of the sample may vary within the above range depending on needs.

The pressure may be controlled by the rod 11 of the motor 2 and the rod 11 according to the present invention. For example, pressure may be controlled using a stepping motor. In some occasions, manual or automotive control is possible. The pressure controlled to a range of 0~30 kgf/cm$^2$ by the rod 11 is displayed on the load indicator.

The control box 1 includes the load indicator, the differential pressure gauge, the motor speed controller, and the load controller. The load indicator shows the degree of pressure presently being applied, and the differential pressure gauge indicates the difference between the pressure of the gas before passing through the through-plane of the sample or through the in-plane of the sample and the atmospheric pressure after the gas is passed through the sample.

Figure 3:
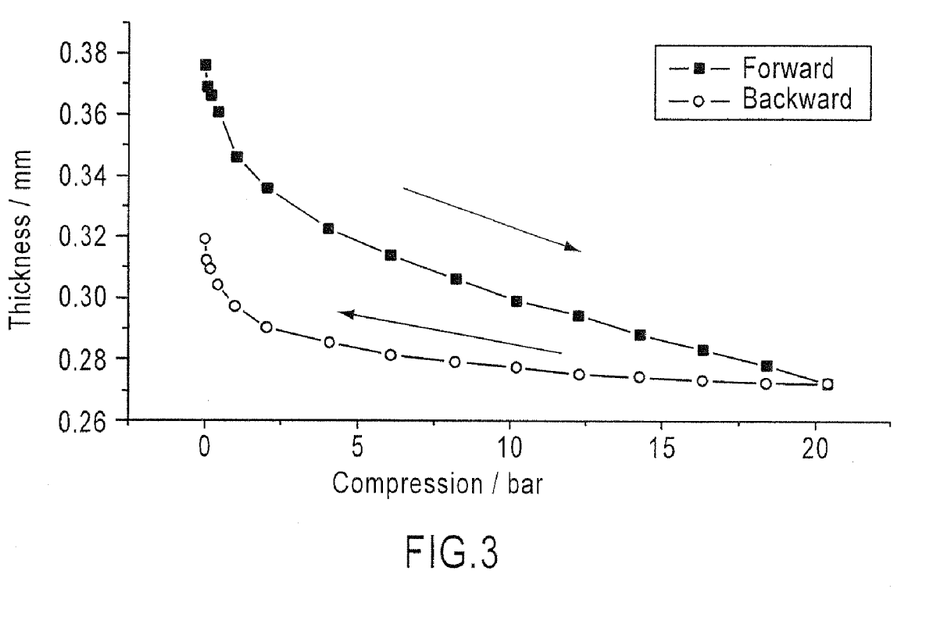
FIG. 3 is a graph showing changes in thickness depending on compression pressure measured using the system according to the present invention.

FIG. 3 is a graph showing changes in thickness of the sample depending on the compression pressure, measured using the system according to the present invention. Because the gas diffusion layer is not a perfect elastic body, when pressure is applied once to the gas diffusion layer, the thickness of the gas diffusion layer is not restored to the initial value even after removal of the pressure. Hence, the varying thickness of the sample upon the application of the pressure (forward) does not agree with the varying thickness of the sample upon the removal of the pressure (backward). Upon actual stack clamping, assembling and disassembling are repeated, and thus it is important to find thickness-change cycle data depending on the pressure.

Figure 4:
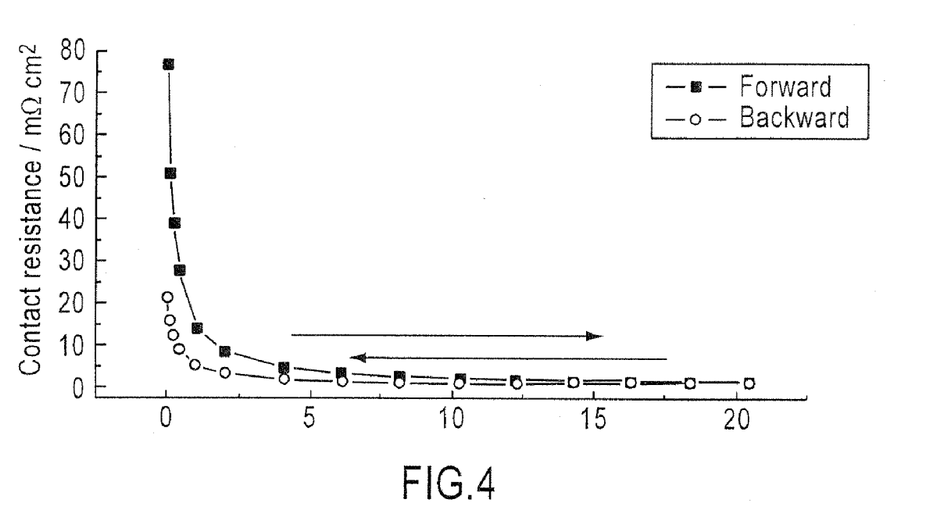
FIG. 4 is a graph showing changes in contact resistance depending on the compression pressure measured using the system according to the present invention.

FIG. 4 is a graph showing changes in contact resistance of the sample depending on the compression pressure measured using the system of the present invention. As shown in this drawing, the contact resistance is drastically reduced in the low pressure range and is then not greatly changed at a pressure of 5 bar or more. Due to damage to the structure of the gas diffusion layer by clamping pressure, even after the pressure is removed, it can be seen that the initial value is not obtained.

Figure 5:
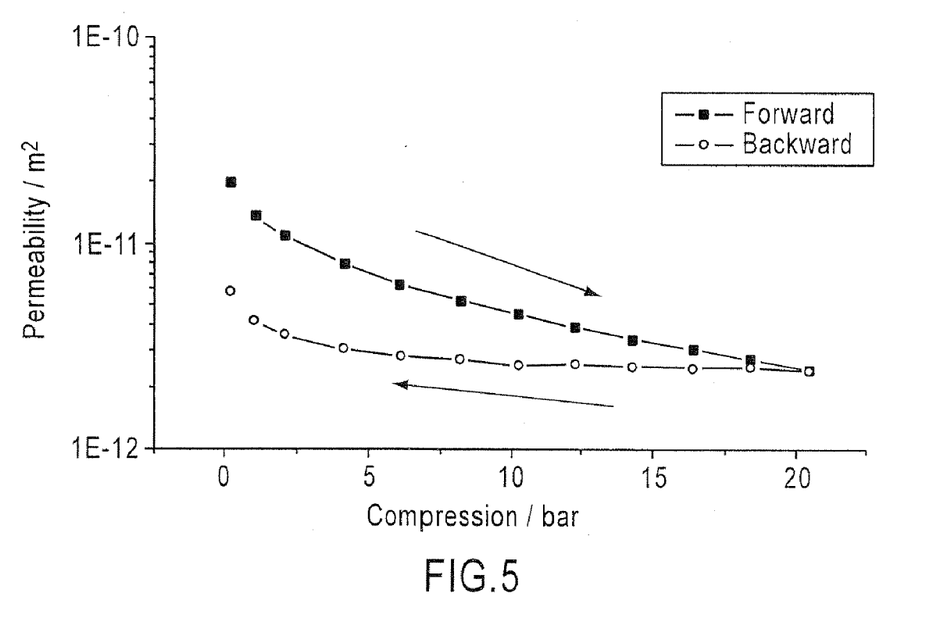
FIG. 5 is a graph showing in-plane permeability depending on the compression pressure measured using the system according to the present invention.

FIG. 5 shows in-plane permeability depending on the compression pressure measured using the system according to the present invention. The values of thickness and differential pressure are substituted into an equation according to Darcy's law, thus calculating gas permeability.

Darcy's Law $$u_g = -\frac{k_g}{\mu_g} \nabla P_g$$

In the drawing, 1 bar represents 100000 Pa.

Also, $u_g$ is represented by Q/A. The flow rate is controlled using an MFC, thus obtaining a Q value, and the sectional area A of the sample varies depending on the change in the thickness. Further, $\mu_g$ is a viscosity of the gas used, and $\nabla P_g$ is the difference between the corresponding pressure and the pressure at the flow rate. The axis y of the graph, namely, permeability/m$^2$, is a calculated value corresponding to $k_g$ in the equation according to Darcy's law. As the sample is compressed (forward), the sectional area through which the gas is passed is reduced, and thus the gas permeability is also reduced. Due to damage to the structure of the gas diffusion layer by clamping pressure, even after the pressure is removed (backward), the initial value is not obtained.

Figure 6:
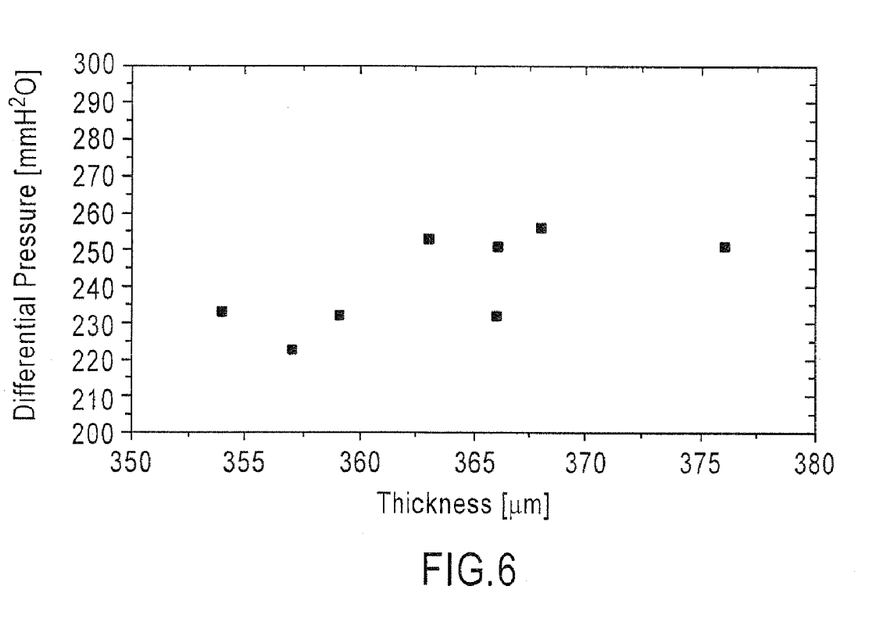
FIG. 6 is a graph showing thickness and differential pressure for the through-plane of eight 10BA gas diffusion layer samples available from SGL, measured using the system according to the present invention.

FIG. 6 is a graph showing thickness and differential pressure for the through-plane of each of 8 Sigracet® SGL10BA gas diffusion layer samples, measured using the system according to the present invention. As shown in the graph, the variation in thickness in similar kinds of gas diffusion layers may be seen. As the thickness is reduced, the differential pressure at both ends of the sample is low. In contrast, as the thickness is increased, the differential pressure is increased.

Figure 7:
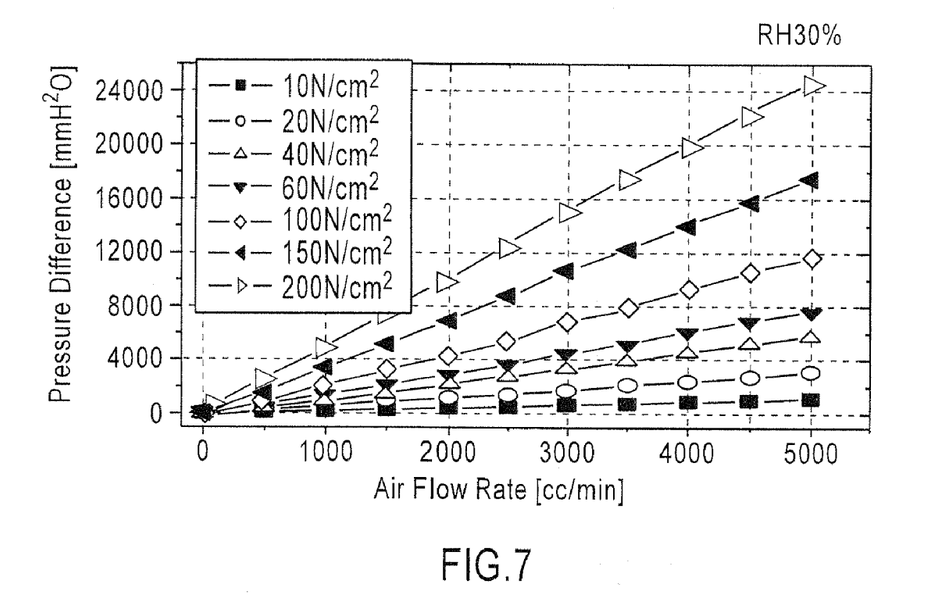
FIG. 7 is a graph showing the differential pressure (in-plane permeability) versus the flow rate depending on the pressure under RH 30%, measured using the system according to the present invention.
Figure 8:
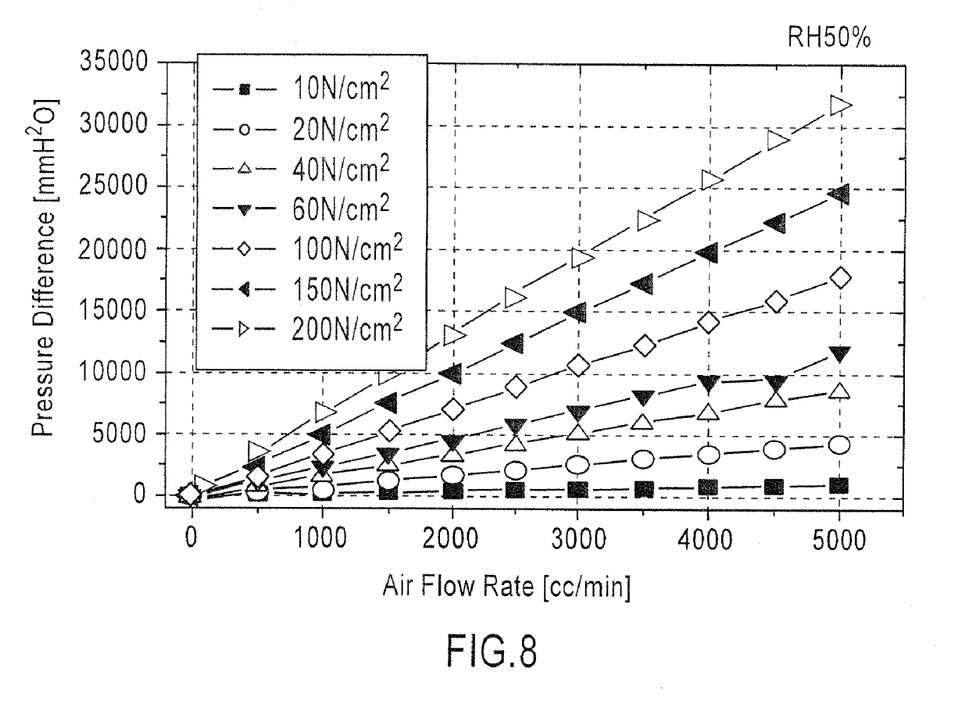
FIG. 8 is a graph showing the differential pressure (in-plane permeability) versus the flow rate depending on the pressure under RH 50%, measured using the system according to the present invention.

FIG. 7 shows in-plane permeability versus the flow rate depending on the pressure under relative humidity (RH 30%) controlled using the device according to the present invention, and FIG. 8 shows in-plane permeability versus the flow rate depending on the pressure under relative humidity (RH 50%) controlled using the device according to the present invention.

A better understanding of the present invention may be obtained through the following examples which are set forth to illustrate, but are not to be construed as limiting the present invention.

EXAMPLE 1

To measure through-plane permeability, a sample was punched using a circular punch having a semi-diameter of 2.5 cm. In this case, a Sigracet® SGL10BA gas diffusion layer was used.

An initial thickness was measured through the following procedures.

1) Depending on material properties of a sample, a standard thickness at a predetermined pressure is determined.

2) In the case of a gas diffusion layer, according to DIN 53855 a thickness under pressure of 25 kPa is determined as an initial thickness, 3) When a load of 25 kPa is applied, the plate 6 descends and upper and lower gold-plated sheets come into contact with each other, and thus the extent of plate movement is shown on a thickness gauge.

4) The thickness value shown on the gauge is set to zero.

5) The motor is switched to rotate in the reverse direction, thus removing the applied pressure.

6) The sample is disposed between the upper and lower gold plated sheets.

7) When a load of 25 kPa is applied, the thickness of the sample is displayed on the gauge.

The upper gold plated sheet was moved downwards, and thus a pressure of 10 bar was applied to the sample. The value of contact resistance displayed on a milliohm meter at the corresponding pressure was detected. The gas was supplied at a flow rate of 100 cc/min.

<Result>
Initial Thickness: 0.370 mm
Contact Resistance: 76 mΩ cm$^2$
Gas Permeability: $4.5*10^{-12}$ m$^2$
Thickness at 10 bar: 0.336 mm
Contact Resistance: 4 mΩ cm$^2$
Gas Permeability: $3.42*10^{-12}$ m$^2$

EXAMPLE 2

To measure in-plane permeability under RH 100% or more, a doughnut-shaped sample was prepared using a circular punch having an inner diameter of 0.85 cm and an outer diameter of 1.5 cm. A Sigracet® SGL35BC gas diffusion layer was located on a position mark of a lower gold plated sheet. An O-ring having a semi-diameter of 2.8 cm was disposed. An initial thickness was determined using the method of Example 1. The temperature of a water bath was set to 60° C., and the upper gold-plated sheet was also sufficiently immersed therein. A predetermined period of time (30 min or longer) was allowed to pass until the upper and lower gold plated sheets and the gas diffusion layer therebetween all achieved thermal equilibrium at 60° C. The temperature of the supplied moisture gas was set to 70° C., such that the relative humidity was 126%. A pressure as high as 10 bar was applied. The flow rate was 200, 400, 600, and 800 cc/min. In this case, because the relative humidity was greater than 100%, the inside of the gas diffusion layer was in a two-phase state. The differential pressure of the sample was measured over time.

Figure 9:
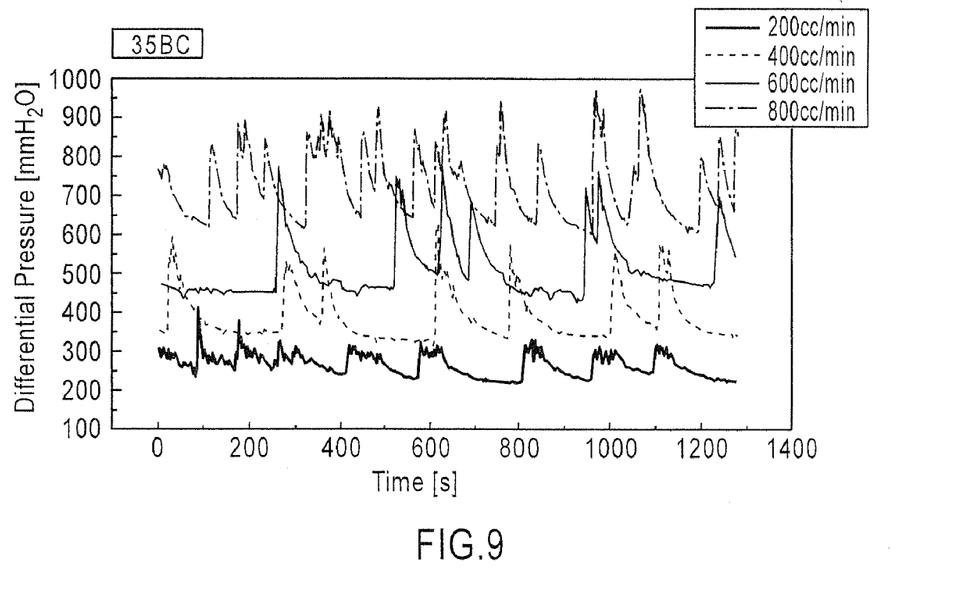
FIG. 9 is a graph showing changes in differential pressure over time in Example 2.

As shown in FIG. 9 which is a graph of changes in the differential pressure over time, when the gas is passed through the in-plane of the sample, a water transfer mechanism may be expected to occur, in which the differential pressure is increased when water prevents the flow of the gas in the gas diffusion layer, whereas the differential pressure is reduced when water is removed by the supplied gas.

As described hereinbefore, the present invention provides an integrated multi-measurement system for simultaneously measuring physical properties of a gas diffusion layer for a polymer electrolyte fuel cell with respect to compression. To evaluate the physical properties of the gas diffusion layer under actual clamping conditions is essential when designing and manufacturing a fuel cell stack. Thus, according to the present invention, upon measurement of the physical properties of the gas diffusion layer of the fuel cell, changes in the physical properties (thickness, contact resistance, gas permeability and so on) depending on clamping pressure can be simultaneously measured. Also, the temperature of the integrated multi-measurement system for measuring the physical properties of the gas diffusion layer of the fuel cell can be controlled, and thus differential pressure of the gas diffusion layer depending on relative humidity can be measured. Based on accurate values of the physical properties, the clamping conditions of the fuel cell can be optimized, and two-phase flow in the gas diffusion layer can be understood. Further, the effect of bypass flow into the gas diffusion layer onto performance of the fuel cell can be ascertained, thus making it possible to design and manufacture a separator for uniform gas distribution. Thereby, the measurement system according to the present invention is expected to have high industrial applicability.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An integrated multi-measurement system for measuring physical properties including thickness, electrical resistance and differential pressure of a gas diffusion layer for a polymer electrolyte fuel cell with respect to compression, comprising:
   a motor and a rod for applying pressure to a gas diffusion layer sample;
   a plate descending by the pressure applied by the motor and the rod;
   a thickness gauge fixed on the plate and measuring a change in thickness of the gas diffusion layer sample depending on the pressure;
   an upper plated sheet which is pressed at an upper surface thereof by the plate and which comes into contact with a lower portion of the plate descending by the pressure applied by the motor and the rod to thus press the gas diffusion layer sample located under the upper plated sheet, the upper plated sheet having gas outlets formed in one or more surfaces of the upper plated sheet to discharge a gas passed through the gas diffusion layer sample to outside via an internal passage and a milliohm meter connection terminal formed at a position of a plated surface of the upper plated sheet;
   a lower plated sheet located under the upper plated sheet to thus support the pressure applied to the gas diffusion layer sample and having a gas inlet formed in one surface of the lower plated sheet to supply the gas to the gas diffusion layer sample so that the gas is discharged to the gas diffusion layer sample via an internal passage and a milliohm meter connection terminal formed at a position of the lower plated sheet;
   a milliohm meter wire-connected to the milliohm meter connection terminals respectively mounted to the upper plated sheet and the lower plated sheet so as to measure electrical resistance; and
   a control box including a load indicator, a motor speed controller, a load controller, and a differential pressure gauge for measuring differential pressure for an in-plane and a through-plane of the gas diffusion layer sample pressed by the motor and the rod.

2. The integrated multi-measurement system as set forth in claim 1, wherein the gas outlets of the upper plated sheet include a pair of gas outlets provided at both sides of the upper plated sheet such that the differential pressure for the through-plane of the gas diffusion layer sample is measured by opening of one of the pair of gas outlets and the differential pressure for the in-plane of the gas diffusion layer sample is measured by opening of the other of the pair of gas outlets.

3. The integrated multi-measurement system as set forth in claim 1, wherein the upper plated sheet and the lower plated sheet are plated with gold.

4. The integrated multi-measurement system as set forth in claim 1, further comprising a device for controlling a temperature outside of the upper plated sheet and the lower plated sheet between which the gas diffusion layer is disposed, so as to measure the differential pressure depending on relative humidity.

5. The integrated multi-measurement system as set forth in claim 4, wherein a sealing member including an O-ring is mounted around the gas diffusion layer sample disposed between the upper plated sheet and the lower plated sheet.

6. The integrated multi-measurement system as set forth in claim 4, wherein the device for controlling a temperature applied to the upper plated sheet and the lower plated sheet comprises one or more selected from among a thermostat water bath, a thermostat bath, a heating tape, and a heating band.

7. The integrated multi-measurement system as set forth in claim 1, wherein the lower plated sheet has a position mark for locating the gas diffusion layer sample thereon and additionally has an acrylic sheet having a semicircular shape used as a jig for more accurate alignment so that the sample is located accurately at a position.

8. The integrated multi-measurement system as set forth in claim 1, wherein the thickness gauge has a resolution of 0.001 mm (1 μm) or more.

9. The integrated multi-measurement system as set forth in claim 1, wherein the gas diffusion layer sample disposed between the upper plated sheet and the lower plated sheet is sized to have an outer diameter of 0.5~5 cm and an inner diameter of 0.3~4.5 cm.

10. The integrated multi-measurement system as set forth in claim 1, wherein the motor and the rod control the pressure to 0~30 kgf/cm$^2$ using a stepping motor.

* * * * *